US012807979B2

(12) United States Patent

Lee et al.

(10) Patent No.: US 12,807,979 B2

(45) Date of Patent: Nov. 24, 2026

(54) MODIFIED POLYPEPTIDE HAVING LYSOZYME ACTIVITY

(71) Applicant: CJ CHEILJEDANG CORPORATION, Seoul (KR)

(72) Inventors: Kyung-Chang Lee, Seoul (KR); Jihyun Shim, Seoul (KR); Jae Yong Park, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 472 days.

(21) Appl. No.: 18/558,904

(22) PCT Filed: Mar. 2, 2022

(86) PCT No.: PCT/KR2022/002898

§ 371 (c)(1),
(2) Date: Nov. 3, 2023

(87) PCT Pub. No.: WO2022/234937

PCT Pub. Date: Nov. 10, 2022

(65) Prior Publication Data

US 2024/0218413 A1 Jul. 4, 2024

(30) Foreign Application Priority Data

May 7, 2021 (KR) ........................ 10-2021-0059347

(51) Int. Cl.

| | |
|---|---|
| ***C12P 21/06*** | (2006.01) |
| ***A01N 63/50*** | (2020.01) |
| ***A01P 1/00*** | (2006.01) |
| ***C07K 14/37*** | (2006.01) |
| ***C12N 9/36*** | (2006.01) |
| ***C12N 15/81*** | (2006.01) |
| ***C12R 1/645*** | (2006.01) |
| ***C12R 1/84*** | (2006.01) |

(52) U.S. Cl.

CPC .............. *C12P 21/06* (2013.01); *A01N 63/50* (2020.01); *A01P 1/00* (2021.08); *C12N 9/2462* (2013.01); *C12Y 302/01017* (2013.01)

(58) Field of Classification Search

None

See application file for complete search history.

(56) References Cited

U.S. PATENT DOCUMENTS

| | | | | |
|---|---|---|---|---|
| 11,896,033 B2 * | 2/2024 | Klausen | ................ | A23K 50/30 |
| 2020/0131492 A1 | 4/2020 | Liu et al. | | |

FOREIGN PATENT DOCUMENTS

| | | |
|---|---|---|
| CN | 111607582 A | 9/2020 |
| JP | 2013-520189 A | 6/2013 |
| WO | 2011/104339 A1 | 9/2011 |
| WO | 2018/113743 A1 | 6/2018 |
| WO | 2018/113745 A1 | 6/2018 |

OTHER PUBLICATIONS

International Search Report issued in corresponding International Patent Application No. PCT/KR2022/002898 dated Jun. 9, 2022.
NCBI, GenBank Accession No. OBT62547.1, 'hypothetical protein VE03_07401 [*Pseudogymnoascus* sp. 23342-1-I1]', 3 pages, (Jun. 24, 2016).
NCBI, GenBank Accession No. KFY23058.1, 'hypothetical protein V493_06130 [*Pseudogymnoascus* sp. VKM F-4281 (FW-2241)]', 3 pages, (Sep. 9, 2014).
Proctor et al., "The chemistry of lysozyme and its use as a food preservative and a pharmaceutical", C R C Critical Reviews in Food Science and Nutrition, vol. 26, Issue 4, 1998, pp. 359-395.
Extended European Search Report issued in corresponding European Patent Application No. 22798983.7, dated Jul. 2, 2025.
Notice of Allowance issued in corresponding Korean Patent Application No. 10-2021-0059347, dated Sep. 4, 2024.

* cited by examiner

*Primary Examiner* — Manjunath N Rao
*Assistant Examiner* — Jae W Lee
(74) *Attorney, Agent, or Firm* — Morgan, Lewis & Bockius LLP

(57) ABSTRACT

The present disclosure relates to a modified polypeptide with at least one modification selected from the group consisting of deletion, insertion, and substitution of one or more amino acids at positions corresponding to positions 135 and 202 of SEQ ID NO: 1, and methods of use thereof.

9 Claims, 1 Drawing Sheet

Specification includes a Sequence Listing.

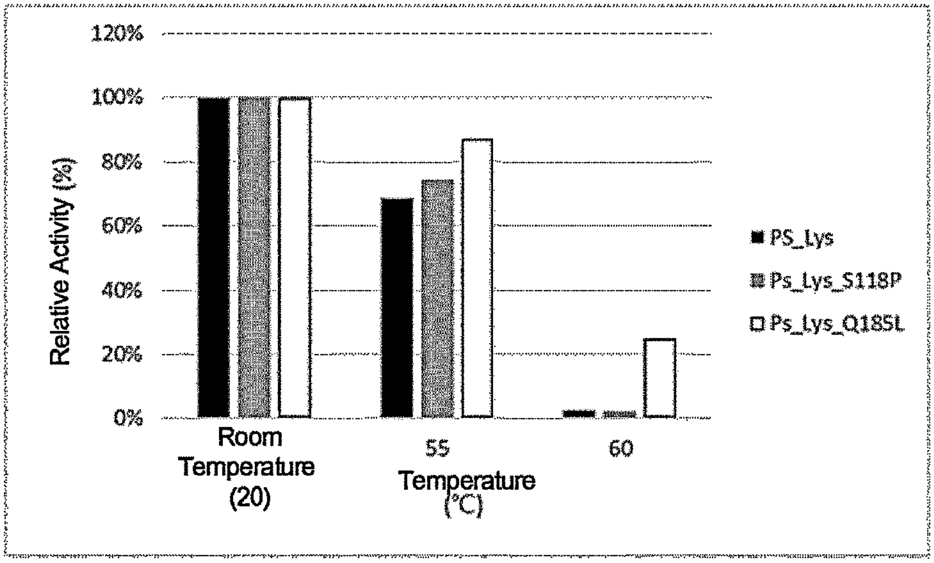
120%
100%
80%
60%
40%
20%
0%
Relative Activity (%)
Room Temperature (20)
55
60
Temperature (°C)
PS_Lys
Ps_Lys_S118P
Ps_Lys_Q185L
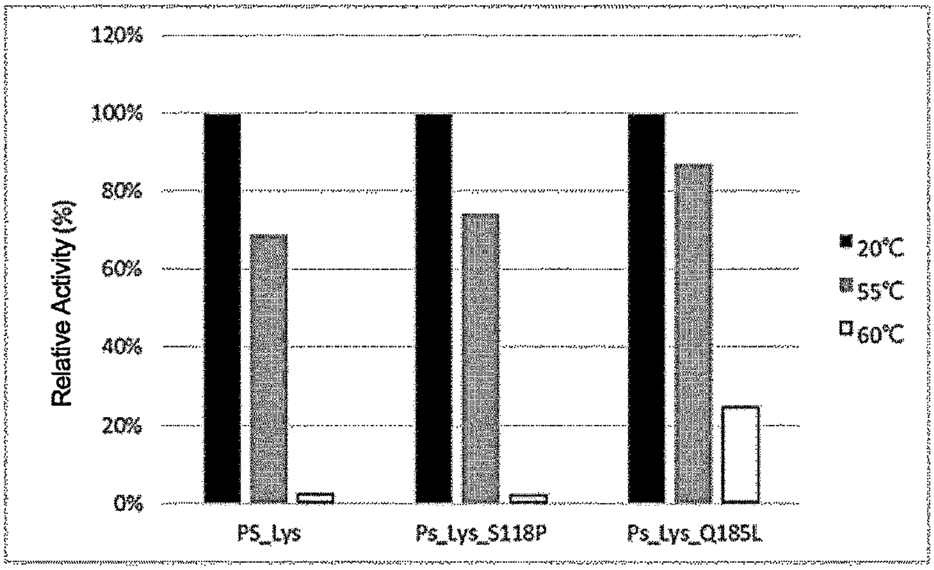
120%
100%
80%
60%
40%
20%
0%
Relative Activity (%)
PS_Lys
Ps_Lys_S118P
Ps_Lys_Q185L
20°C
55°C
60°C

SEQUENCE LISTING

```
<160> NUMBER OF SEQ ID NOS: 14

<210> SEQ ID NO 1
<211> LENGTH: 233
<212> TYPE: PRT
<213> ORGANISM: Artificial Sequence
<220> FEATURE:
<223> OTHER INFORMATION: Ps_Lys_nt

<400> SEQUENCE: 1

Met Lys Phe Ser Ser Leu Val Val Ala Ser Ile Leu Gly Phe Ala Ala
1               5                   10                  15

Ala Thr Pro Ala Ser Leu Glu Lys Arg Ala Thr Val Gln Gly Phe Asp
            20                  25                  30

Ile Ser Gly Tyr Gln Pro Thr Val Asp Phe Ala Gly Ala Tyr Ala Ser
        35                  40                  45

Gly Ala Arg Phe Val Ile Ile Lys Ala Thr Glu Gly Thr Ser Tyr Lys
    50                  55                  60

Ser Pro Val Phe Ser Ser Gln Tyr Thr Gly Ala Thr Lys Ala Gly Phe
65                  70                  75                  80

Ile Arg Gly Ala Tyr His Phe Ala His Pro Gly Ser Ser Ser Gly Ala
                85                  90                  95

Ala Gln Ala Asn Tyr Phe Leu Ala Asn Gly Gly Gly Trp Ser Lys Asp
            100                 105                 110

Gly Ile Thr Leu Pro Gly Met Leu Asp Ile Glu Tyr Asn Pro Ser Gly
        115                 120                 125

Ala Thr Cys Phe Gly Ile Ser Gln Ser Ala Met Val Ala Trp Ile Lys
    130                 135                 140

Asp Phe Val Asn Thr Tyr His Thr Lys Thr Gly Val Tyr Pro Leu Ile
145                 150                 155                 160

Tyr Thr Thr Thr Asp Trp Trp Thr Gln Cys Thr Gly Asn Asn Ala Ser
                165                 170                 175

Phe Gly Ser Thr Cys Pro Leu Val Leu Ala Arg Tyr Ser Thr Ser Pro
            180                 185                 190

Gly Thr Met Pro Ala Gly Trp Ala Phe Gln Thr Ile Trp Gln Asn Asn
        195                 200                 205

Asp Ala Tyr Lys Tyr Gly Gly Asp Ser Asp Ile Phe Asn Gly Ser Leu
    210                 215                 220

Asp Gln Leu Lys Lys Ile Ala Leu Gly
225                 230


<210> SEQ ID NO 2
<211> LENGTH: 699
<212> TYPE: DNA
<213> ORGANISM: Artificial Sequence
<220> FEATURE:
<223> OTHER INFORMATION: Ps_Lys_nt
```

<400> SEQUENCE: 2
atgaagttct cgagtcttgt cgtcgcgtcc attcttggat tcgccgccgc tacacctgct 60
tcacttgaga agcgggccac ggtgcagggt ttcgacatat cgggttacca accgacggtg 120
gacttcgcgg gtgcatacgc ttcgggggcg agattcgtca tcataaaagc aaccgaaggc 180
acgtcttata aatcgcctgt attctcctcc caatacacag gtgcaactaa agccggattt 240
atcagaggcg cgtatcactt tgcccacccc ggaagttcga gtggagcagc ccaggccaac 300
tactttctgg caaacggtgg aggatggagc aaagacggca taacgttgcc ggggatgctg 360
gatatcgagt acaatccgtc gggggccacc tgtttcggta tatcacagtc ggcaatggtt 420
gcatggatta aggacttcgt gaacacttac catacaaaaa ccggagttta cccgttgata 480
tatactacca ccgactggtg gactcagtgc acggggaata acgcatcgtt cgggtcgaca 540
tgcccgttag tcttggcacg gtattctaca tccccaggta cgatgccagc agggtgggcg 600
tttcaaacaa tatggcagaa taatgatgct tacaagtatg gcggtgattc agacattttc 660
aacggctctc tggatcagct taaaaagatc gcgcttggt 699

<210> SEQ ID NO 3
<211> LENGTH: 216
<212> TYPE: PRT
<213> ORGANISM: Artificial Sequence
<220> FEATURE:
<223> OTHER INFORMATION: Ps_Lys_mature

<400> SEQUENCE: 3

Thr Pro Ala Ser Leu Glu Lys Arg Ala Thr Val Gln Gly Phe Asp Ile
1 5 10 15

Ser Gly Tyr Gln Pro Thr Val Asp Phe Ala Gly Ala Tyr Ala Ser Gly
20 25 30

Ala Arg Phe Val Ile Ile Lys Ala Thr Glu Gly Thr Ser Tyr Lys Ser
35 40 45

Pro Val Phe Ser Ser Gln Tyr Thr Gly Ala Thr Lys Ala Gly Phe Ile
50 55 60

Arg Gly Ala Tyr His Phe Ala His Pro Gly Ser Ser Ser Gly Ala Ala
65 70 75 80

Gln Ala Asn Tyr Phe Leu Ala Asn Gly Gly Gly Trp Ser Lys Asp Gly
85 90 95

Ile Thr Leu Pro Gly Met Leu Asp Ile Glu Tyr Asn Pro Ser Gly Ala
100 105 110

Thr Cys Phe Gly Ile Ser Gln Ser Ala Met Val Ala Trp Ile Lys Asp
115 120 125

Phe Val Asn Thr Tyr His Thr Lys Thr Gly Val Tyr Pro Leu Ile Tyr
130 135 140

Thr Thr Thr Asp Trp Trp Thr Gln Cys Thr Gly Asn Asn Ala Ser Phe
145 150 155 160

Gly Ser Thr Cys Pro Leu Val Leu Ala Arg Tyr Ser Thr Ser Pro Gly
165 170 175

Thr Met Pro Ala Gly Trp Ala Phe Gln Thr Ile Trp Gln Asn Asn Asp
180 185 190

Ala Tyr Lys Tyr Gly Gly Asp Ser Asp Ile Phe Asn Gly Ser Leu Asp
195 200 205

Gln Leu Lys Lys Ile Ala Leu Gly
210 215

<210> SEQ ID NO 4
<211> LENGTH: 24
<212> TYPE: DNA
<213> ORGANISM: Artificial Sequence
<220> FEATURE:
<223> OTHER INFORMATION: PICZ_F

<400> SEQUENCE: 4
tgagtttgta gccttagaca tgac 24

<210> SEQ ID NO 5
<211> LENGTH: 21
<212> TYPE: DNA
<213> ORGANISM: Artificial Sequence
<220> FEATURE:
<223> OTHER INFORMATION: PICZ_R

<400> SEQUENCE: 5
agcttcagcc tctcttttct c 21

<210> SEQ ID NO 6
<211> LENGTH: 37
<212> TYPE: DNA
<213> ORGANISM: Artificial Sequence
<220> FEATURE:
<223> OTHER INFORMATION: Ps_Lys_F1

<400> SEQUENCE: 6
aagagaggct gaagctacac ctgcttcact tgagaag 37

<210> SEQ ID NO 7
<211> LENGTH: 37
<212> TYPE: DNA
<213> ORGANISM: Artificial Sequence
<220> FEATURE:
<223> OTHER INFORMATION: Ps_Lys_R1

<400> SEQUENCE: 7
taaggctaca aactcaacca agcgcgatct ttttaag 37

<210> SEQ ID NO 8
<211> LENGTH: 22
<212> TYPE: DNA
<213> ORGANISM: Artificial Sequence
<220> FEATURE:
<223> OTHER INFORMATION: S118P_F

<400> SEQUENCE: 8
gtttcggtat accacagtcg gc 22

<210> SEQ ID NO 9
<211> LENGTH: 22
<212> TYPE: DNA
<213> ORGANISM: Artificial Sequence
<220> FEATURE:
<223> OTHER INFORMATION: S118P_R

<400> SEQUENCE: 9
gccgactgtg gtataccgaa ac 22

<210> SEQ ID NO 10
<211> LENGTH: 22
<212> TYPE: DNA
<213> ORGANISM: Artificial Sequence
<220> FEATURE:
<223> OTHER INFORMATION: Q185L_F

<400> SEQUENCE: 10
gtgggcgttt ttgacaatat gg 22

<210> SEQ ID NO 11
<211> LENGTH: 22
<212> TYPE: DNA
<213> ORGANISM: Artificial Sequence
<220> FEATURE:
<223> OTHER INFORMATION: Q185L_R

<400> SEQUENCE: 11
ccatattgtc aaaaacgccc ac 22

<210> SEQ ID NO 12
<211> LENGTH: 216
<212> TYPE: PRT
<213> ORGANISM: Artificial Sequence
<220> FEATURE:
<223> OTHER INFORMATION: Ps_Lys_Mature S118P

<400> SEQUENCE: 12

```
Thr Pro Ala Ser Leu Glu Lys Arg Ala Thr Val Gln Gly Phe Asp Ile
1               5                   10                  15

Ser Gly Tyr Gln Pro Thr Val Asp Phe Ala Gly Ala Tyr Ala Ser Gly
            20                  25                  30

Ala Arg Phe Val Ile Ile Lys Ala Thr Glu Gly Thr Ser Tyr Lys Ser
        35                  40                  45

Pro Val Phe Ser Ser Gln Tyr Thr Gly Ala Thr Lys Ala Gly Phe Ile
    50                  55                  60

Arg Gly Ala Tyr His Phe Ala His Pro Gly Ser Ser Ser Gly Ala Ala
65                  70                  75                  80

Gln Ala Asn Tyr Phe Leu Ala Asn Gly Gly Gly Trp Ser Lys Asp Gly
                85                  90                  95

Ile Thr Leu Pro Gly Met Leu Asp Ile Glu Tyr Asn Pro Ser Gly Ala
            100                 105                 110

Thr Cys Phe Gly Ile Pro Gln Ser Ala Met Val Ala Trp Ile Lys Asp
        115                 120                 125

Phe Val Asn Thr Tyr His Thr Lys Thr Gly Val Tyr Pro Leu Ile Tyr
    130                 135                 140

Thr Thr Thr Asp Trp Trp Thr Gln Cys Thr Gly Asn Asn Ala Ser Phe
145                 150                 155                 160

Gly Ser Thr Cys Pro Leu Val Leu Ala Arg Tyr Ser Thr Ser Pro Gly
                165                 170                 175

Thr Met Pro Ala Gly Trp Ala Phe Gln Thr Ile Trp Gln Asn Asn Asp
            180                 185                 190

Ala Tyr Lys Tyr Gly Gly Asp Ser Asp Ile Phe Asn Gly Ser Leu Asp
        195                 200                 205

Gln Leu Lys Lys Ile Ala Leu Gly
    210                 215
```

<210> SEQ ID NO 13
<211> LENGTH: 216
<212> TYPE: PRT
<213> ORGANISM: Artificial Sequence
<220> FEATURE:
<223> OTHER INFORMATION: Ps_Lys_Mature Q185L

<400> SEQUENCE: 13

```
Thr Pro Ala Ser Leu Glu Lys Arg Ala Thr Val Gln Gly Phe Asp Ile
1               5                   10                  15

Ser Gly Tyr Gln Pro Thr Val Asp Phe Ala Gly Ala Tyr Ala Ser Gly
            20                  25                  30

Ala Arg Phe Val Ile Ile Lys Ala Thr Glu Gly Thr Ser Tyr Lys Ser
        35                  40                  45

Pro Val Phe Ser Ser Gln Tyr Thr Gly Ala Thr Lys Ala Gly Phe Ile
    50                  55                  60

Arg Gly Ala Tyr His Phe Ala His Pro Gly Ser Ser Ser Gly Ala Ala
65                  70                  75                  80

Gln Ala Asn Tyr Phe Leu Ala Asn Gly Gly Gly Trp Ser Lys Asp Gly
                85                  90                  95

Ile Thr Leu Pro Gly Met Leu Asp Ile Glu Tyr Asn Pro Ser Gly Ala
            100                 105                 110

Thr Cys Phe Gly Ile Ser Gln Ser Ala Met Val Ala Trp Ile Lys Asp
        115                 120                 125

Phe Val Asn Thr Tyr His Thr Lys Thr Gly Val Tyr Pro Leu Ile Tyr
    130                 135                 140

Thr Thr Thr Asp Trp Trp Thr Gln Cys Thr Gly Asn Asn Ala Ser Phe
145                 150                 155                 160

Gly Ser Thr Cys Pro Leu Val Leu Ala Arg Tyr Ser Thr Ser Pro Gly
                165                 170                 175

Thr Met Pro Ala Gly Trp Ala Phe Leu Thr Ile Trp Gln Asn Asn Asp
            180                 185                 190

Ala Tyr Lys Tyr Gly Gly Asp Ser Asp Ile Phe Asn Gly Ser Leu Asp
        195                 200                 205

Gln Leu Lys Lys Ile Ala Leu Gly
    210                 215


<210> SEQ ID NO 14
<211> LENGTH: 216
<212> TYPE: PRT
<213> ORGANISM: Artificial Sequence
<220> FEATURE:
<223> OTHER INFORMATION: Ps_Lys_Mature S118P+Q185L

<400> SEQUENCE: 14

Thr Pro Ala Ser Leu Glu Lys Arg Ala Thr Val Gln Gly Phe Asp Ile
1               5                   10                  15

Ser Gly Tyr Gln Pro Thr Val Asp Phe Ala Gly Ala Tyr Ala Ser Gly
            20                  25                  30

Ala Arg Phe Val Ile Ile Lys Ala Thr Glu Gly Thr Ser Tyr Lys Ser
        35                  40                  45

Pro Val Phe Ser Ser Gln Tyr Thr Gly Ala Thr Lys Ala Gly Phe Ile
    50                  55                  60

Arg Gly Ala Tyr His Phe Ala His Pro Gly Ser Ser Ser Gly Ala Ala
65                  70                  75                  80

Gln Ala Asn Tyr Phe Leu Ala Asn Gly Gly Gly Trp Ser Lys Asp Gly
                85                  90                  95

Ile Thr Leu Pro Gly Met Leu Asp Ile Glu Tyr Asn Pro Ser Gly Ala
            100                 105                 110

Thr Cys Phe Gly Ile Pro Gln Ser Ala Met Val Ala Trp Ile Lys Asp
        115                 120                 125

Phe Val Asn Thr Tyr His Thr Lys Thr Gly Val Tyr Pro Leu Ile Tyr
    130                 135                 140
```

-continued

```
Thr Thr Thr Asp Trp Trp Thr Gln Cys Thr Gly Asn Asn Ala Ser Phe
145                 150                 155                 160

Gly Ser Thr Cys Pro Leu Val Leu Ala Arg Tyr Ser Thr Ser Pro Gly
                165                 170                 175

Thr Met Pro Ala Gly Trp Ala Phe Leu Thr Ile Trp Gln Asn Asn Asp
            180                 185                 190

Ala Tyr Lys Tyr Gly Gly Asp Ser Asp Ile Phe Asn Gly Ser Leu Asp
        195                 200                 205

Gln Leu Lys Lys Ile Ala Leu Gly
    210                 215
```

MODIFIED POLYPEPTIDE HAVING LYSOZYME ACTIVITY

A computer readable text file, entitled "133660-04-9018-US_Sequence_Listing_ST25.txt," created on or about Nov. 3, 2023, with a file size of 12,628 bytes contains the sequence listing for this application and is hereby incorporated by reference in its entirety.

TECHNICAL FIELD

The present disclosure relates to a modified polypeptide having lysozyme activity and use thereof.

BACKGROUND ART

Lysozyme is a glycosyl hydrolase that cleaves the glycosidic bond of peptidoglycan, a component of the cell wall of microorganisms, and has the activity of degrading the β-1,4-glycosidic bond of N-acetylglucosamine and N-acetylmuramic acid (NAM). Lysozyme is used in the production and preservation of feed/food, detergents, quasi-drugs, cosmetics, and pharmaceuticals (Proctor V A, Cunningham F E. The chemistry of lysozyme and its use as a food preservative and a pharmaceutical. *Crit Rev Food Sci Nutr.* 1988; 26(4): 359-95. doi: 10.1080/10408398809527473. PMID: 3280250.).

DISCLOSURE

Technical Problem

For the convenient use of lysozyme employed in various fields, its resistance and activity in harsh conditions (high-temperature environments) are required.

Technical Solution

It is one object of the present disclosure to provide a modified polypeptide having lysozyme activity.

It is another object of the present disclosure to provide a composition including the modified polypeptide.

It is still another object of the present disclosure to provide the use of the modified polypeptide or the composition for the reaction with peptidoglycan.

It is yet another object of the present disclosure to provide a method for hydrolyzing peptidoglycan, including: contacting the modified polypeptide, a host cell expressing the modified polypeptide, and/or a composition including the modified polypeptide with peptidoglycan.

It is even another object of the present disclosure to provide a method for lysing bacteria, including: contacting the modified polypeptide, a host cell expressing the modified polypeptide, and/or a composition including the modified polypeptide with bacteria including peptidoglycan as a component of a cell wall.

It is further another object of the present disclosure to provide a polynucleotide encoding the modified polypeptide; a nucleic acid construct containing the polynucleotide; a vector containing the polynucleotide or the nucleic acid construct; and/or a host cell containing the polynucleotide, the nucleic acid construct or the vector.

It is still further another object of the present disclosure to provide a method for preparing the modified polypeptide.

Advantageous Effects

The modified polypeptide of the present disclosure, which has lysozyme activity, can be effectively used in various industrial fields.

BRIEF DESCRIPTION OF THE DRAWING

FIG. 1 shows the results of confirming the thermal stability of the modified polypeptide of the present disclosure.

DETAILED DESCRIPTION OF PREFERRED EMBODIMENTS

It is one object of the present disclosure to provide a modified polypeptide having lysozyme activity.

It is another object of the present disclosure to provide a composition including the modified polypeptide.

It is still another object of the present disclosure to provide the use of the modified polypeptide or the composition for the reaction with peptidoglycan.

It is yet another object of the present disclosure to provide a method for hydrolyzing peptidoglycan, including: contacting the modified polypeptide, a host cell expressing the modified polypeptide, and/or a composition including the modified polypeptide with peptidoglycan.

It is even another object of the present disclosure to provide a method for lysing bacteria, including: contacting the modified polypeptide, a host cell expressing the modified polypeptide, and/or a composition including the modified polypeptide with bacteria including peptidoglycan as a component of a cell wall.

It is further another object of the present disclosure to provide a polynucleotide encoding the modified polypeptide; a nucleic acid construct containing the polynucleotide; a vector containing the polynucleotide or the nucleic acid construct; and/or a host cell containing the polynucleotide, the nucleic acid construct or the vector.

It is still further another object of the present disclosure to provide a method for preparing the modified polypeptide.

SUMMARY OF THE INVENTION

One aspect of the present disclosure provides a modified polypeptide having lysozyme activity.

In one embodiment, i) the modified polypeptide has a sequence identity of 70% or more and less than 100% with SEQ ID NO: 1; and/or

- ii) the modified polypeptide is a polypeptide encoded by a polynucleotide having a sequence identity of 70% or more and less than 100% with the sequence encoding a mature polypeptide of SEQ ID NO: 1; and/or
- iii) the modified polypeptide is a polypeptide encoded by (a) a mature polypeptide coding sequence of SEQ ID NO: 1, (b) a cDNA thereof, or (c) a polynucleotide that hybridizes to the full-length complement of (a) or (b) under low-stringency conditions, medium-stringency conditions, medium-high-stringency conditions, high-stringency conditions, or very high-stringency conditions; and/or
- iv) the modified polypeptide is a functional fragment of i), ii) or iii) polypeptide having lysozyme activity; and the modified polypeptide includes any one of the modifications selected from below:

deletion of amino acids at one or more of positions 135 and 202, insertion of an amino acid, and substitution with another amino acid, and a combination thereof;

wherein the position number is a position corresponding to the position of the polypeptide of SEQ ID NO: 1.

In one embodiment of any one of the above embodiments, before modification, the amino acid at position 135 may be serine (S); and/or the amino acid at position 202 may be glutamine (Q).

In one embodiment of any one of the above embodiments, the modified polypeptide may include modifications of amino acids at positions selected from i) to iii) below:

i) 135;
ii) 202; and
iii) 135+202;

wherein the position number is a position corresponding to the position of the polypeptide of SEQ ID NO: 1.

In one embodiment of any one of the above embodiments, the modified polypeptide may include any one or more substitutions from i) and ii) below;

i) substitution of an amino acid at position 135 with proline; and
ii) substitution of an amino acid at position 202 with leucine;

wherein the position number is a position corresponding to the position of the polypeptide of SEQ ID NO: 1.

In one embodiment of any one of the above embodiments, the modified polypeptide may include any one or more substitutions selected from below:

S135P;
Q202L; and
S135P+Q202L;

wherein the position number is a position corresponding to the position of the polypeptide of SEQ ID NO: 1.

In one embodiment of any one of the above embodiments, the modified polypeptide may have increased thermal tolerance and/or thermal stability compared to a polypeptide composed of the amino acid sequence of SEQ ID NO: 1.

Another aspect of the present disclosure provides a composition including the modified polypeptide.

Still another aspect of the present disclosure provides the use of the modified polypeptide or the composition including the modified polypeptide for the reaction with peptidoglycan.

Yet another aspect of the present disclosure provides a method for hydrolyzing peptidoglycan, including: contacting the modified polypeptide, a host cell expressing the modified polypeptide, and/or a composition including the modified polypeptide with peptidoglycan.

Even another aspect of the present disclosure provides a method for lysing bacteria, including: contacting the modified polypeptide, a host cell expressing the modified polypeptide, and/or a composition including the modified polypeptide with bacteria including peptidoglycan as a component of a cell wall.

Further another aspect of the present disclosure provides a polynucleotide encoding the modified polypeptide.

Still further another aspect of the present disclosure provides a nucleic acid construct containing the polynucleotide.

Still further another aspect of the present disclosure provides a vector containing the polynucleotide or the nucleic acid construct.

Still further another aspect of the present disclosure provides a host cell containing the polynucleotide, the nucleic acid construct, and/or the vector.

Still further another aspect of the present disclosure provides a method for preparing a modified polypeptide, including culturing the host cell.

MODE FOR CARRYING OUT THE INVENTION

Hereinafter, the present disclosure will be described in detail. Meanwhile, each description and embodiment disclosed herein can be applied to other descriptions and embodiments, respectively. That is, all combinations of various elements disclosed herein fall within the scope of the present disclosure. Further, the scope of the present disclosure is not limited by the specific description described below.

Additionally, those of ordinary skill in the art may be able to recognize or confirm, using only conventional experimentation, many equivalents to the particular aspects of the invention described herein. Furthermore, it is also intended that these equivalents be included in the present disclosure.

As used in the specification and appended claims, the singular forms ("a", "an", and "the") include plural referents unless the context clearly states otherwise. Unless the context indicates otherwise, singular terms shall include the plural and plural terms shall include the singular. As used in the specification and appended claims, unless stated otherwise, the use of "or" may be used to include "and/or".

As used herein, the term "about" may be presented before a particular numerical value. The term "about" used herein includes not only the exact number recited after the term, but also a range that is near or close to that number. Considering the context in which the number is presented, it can be determined whether any number is close to or near the particular number presented. In one example, the term "about" may refer to a range from −10% to +10% of a numerical value. In another example, the term "about" may refer to a range from −5% to +5% of a given numerical value, but is not limited thereto.

As used herein, the descriptions such as the terms "first, second, third, . . . " "i), ii), iii), . . . " or "(a), (b), (c), (d), . . . " are used to distinguish similar constitutions, and these terms do not mean that the constitutions are performed continually or sequentially. For example, when the terms are used in reference to steps of a method, use, or assay, there may be no time interval between these steps, or they may be performed concurrently, or may be performed several seconds, several minutes, several hours, several days, or several months apart.

As used herein, the term "consisting essentially of" may mean that, in the case where the features of the object claimed herein are not substantially affected by the presence of an unspecified component, the unspecified component may be present.

As used herein, the term, "consisting of" means that the total ratio of specific component(s) is 100%. The components or features that are recited after the term "consisting of" may be essential or mandatory. In some embodiments, in addition to the components or features recited after the term "consisting of", any other components or non-essential components may be excluded.

As used herein, the term "comprising/including" means the presence of features, steps or components recited after the term, and does not exclude the presence or addition of one or more features, steps or components. The components or features recited after the term "comprising/including" herein may be essential or mandatory. However, in some embodiments, the term may further include any other or non-essential components or features.

As used herein, the term "comprising/including" may be modified to refer to "consisting essentially of" or "consisting of" in some embodiments.

With respect to amino acid sequences in the present disclosure, although it is described as a polypeptide "comprising/including" an amino acid sequence described by a specific sequence number, a polypeptide "consisting of" an amino acid sequence described by a specific sequence number, or a protein or polypeptide "having" an amino acid sequence described by a specific sequence number, it is apparent that any protein having an amino acid sequence in which part of the sequence is deleted, modified, substituted, conservatively substituted or added can be used in the present disclosure if it has the same or corresponding activity as the polypeptide consisting of the amino acid sequence of the corresponding sequence number. For example, it may be a case where the N-terminus and/or C-terminus of the amino acid sequence is added with a sequence that does not alter the function of the protein, a naturally occurring mutation, a silent mutation thereof, or a conservative substitution, but is not limited thereto.

As used herein, the term "protein" or "polypeptide" refers to a polymer or oligomer of consecutive amino acid residues. In the present disclosure, the "polypeptide", "protein", and "peptide" may be used interchangeably with "amino acid sequence".

In some cases, an amino acid sequence exhibiting activity may be referred to as an "enzyme". In the present disclosure, unless indicated otherwise, amino acid sequences are described in an N-terminus-to-C-terminus direction.

As used herein, the term "recombinant" with respect to a cell, or nucleic acid, polypeptide, or vector indicates that the cell, nucleic acid, polypeptide, or vector has been modified by the introduction of a heterologous nucleic acid or polypeptide or the alteration of a native nucleic acid or polypeptide, or that the cell is derived from a cell thus modified. Therefore, for example, recombinant cells may express genes that are not found within the native (non-recombinant) form of the cells, or may express native genes that are otherwise abnormally expressed, under expressed or not expressed at all.

As used herein, the term "isolated" refers to a substance which exists in a non-naturally occurring environment or does not exist naturally. The term includes substantial isolation of a substance (sequence, enzyme or nucleic acid) from a substance which is naturally associated and found in nature, for example, at least one other component having a sequence, enzyme or nucleic acid.

For example, an isolated sequence, enzyme or nucleic acid provided herein may be provided in a form that is substantially free of one or more contaminants.

Examples of isolated substances include i) any substance that is non-naturally occurring; ii) any substance (e.g., enzyme, variant, nucleic acid, protein, peptide or cofactor) from which one, or more, or all naturally-occurring components associated in nature have been removed; iii) any substance that has been artificially modified from a substance found in nature; or iv) any substance that has been modified to alter the amount of that substance relative to other components associated in nature (e.g., increase in copy number of a gene encoding a specific substance; modification of a promoter naturally linked to a gene encoding a specific substance into a highly active promoter, etc.), but are not limited thereto.

As used herein, the term "wild-type" refers to a naturally-occurring state without artificial modification. When the term "wild-type" is used in reference to a polypeptide, it refers to a naturally occurring polypeptide, which does not have artificial mutations (substitutions, insertions, deletions, etc.) in one or more amino acid positions. Similarly, when the term "wild-type" is used in reference to a polynucleotide, it means not having artificial modifications (substitutions, insertions, deletions) in one or more nucleotides. However, polynucleotides encoding wild-type polypeptides are not limited to wild-type polynucleotides, and include sequences encoding any wild-type polypeptides.

As used herein, the term "parent sequence" or "backbone" refers to a reference sequence in which modification is introduced to create a modified polypeptide. That is, the parent sequence may be served as a starting sequence in which modification such as substitutions, additions, and/or deletions may be introduced. The parent sequence may be naturally-occurring or wild-type, or a variant in which one or more substitutions, insertions or deletions have occurred in the natural or wild type, or may be an artificially synthesized sequence. When the parent sequence is an amino acid sequence exhibiting activity, i.e., an amino acid sequence of an enzyme, it may be referred to as a parent enzyme.

As used herein, the term "reference sequence" means a sequence used to determine the position of amino acids within any amino acid sequence. Any amino acid sequence can be aligned with a reference sequence to determine the position of an amino acid that corresponds to a particular position in the reference sequence within any amino acid sequence.

With respect to amino acid or nucleic acid sequences in the present disclosure, the term "fragment" means a part of a parent sequence. For example, it may be a polypeptide in the form in which one or more amino acids are removed from the C- or N-terminus of the parent sequence.

As used herein, the term "fragment" of an enzyme may refer to a "functional fragment". The "functional fragment" may also be referred to as an active ingredient, and means a polypeptide that is a part of a parent enzyme and has enzymatic activity of the parent enzyme. For example, the functional fragment of an enzyme may include a catalytic site of the enzyme.

The fragment of the enzyme may include a part of the full length of the parent enzyme. For example, the fragment of the enzyme may include amino acids of at least about 20%, 30%, 40%, 50%, 60%, 70%, 80%, 90%, 95%, 98%, 99%, or more, or less than 100% of the full length of the parent enzyme, but is not limited thereto.

As used herein, the term "modifying" means a change or alternation. This may be an alternation from a naturally occurring state. In one example, an enzyme can be altered in such a way that the enzyme is altered from a parent or reference sequence.

In the present disclosure, a modified enzyme may be an enzyme that does not exist as it is in nature, i.e., one which does not occur naturally.

As used herein, the term "modified" means alternation, e.g., from its naturally occurring form. The modified enzyme of the present disclosure includes non-naturally occurring enzymes or naturally occurring variants. In one example, the modified enzyme of the present disclosure is a modified enzyme that has not been found in nature. In one example, the modified enzyme of the present disclosure may not be one occurring spontaneously, but is not limited thereto.

As used herein, the term "modification", when used with respect to amino acid/nucleic acid sequences, may include substitution of an amino acid/nucleic acid residue of a parent sequence for a different amino acid/nucleic acid residue in one or more positions in an amino acid sequence; deletion of an amino acid/nucleic acid residue (or series of amino acid/nucleic acid residues) of a parent sequence in one or more positions; insertion of an amino acid/nucleic acid residue (or series of amino acid/nucleic acid residues) of a parent sequence in one or more positions; truncation of the N-terminal and/or C-terminal amino acid sequences, or 5' and/or 3' nucleic acid sequences, and any combination thereof.

As used herein, the term "variant" or "modified polypeptide" of an enzyme refers to a protein having one or more amino acids different from the parent enzyme by conservative substitution and/or modification. The "variant" or "modified polypeptide" may be used interchangeably. The variant or modified polypeptide may be non-naturally occurring, but is not limited thereto.

The variant differs from the sequence of the parent enzyme by one or more modifications, e.g., substitutions, deletions and/or insertions of amino acids.

Such variants may generally be identified by modifying one or more amino acids from the parent enzyme and evaluating the properties of the modified protein. That is, the ability of the variants may be enhanced, unchanged or reduced relative to the parent enzyme.

Additionally, some variants may include modified polypeptides in which one or more regions, such as an N-terminal leader sequence or transmembrane domain, have been removed.

Further, other variants may include those in which a region has been removed from the N- and/or C-terminus of a mature protein.

The term "variant" or "modified polypeptide" may be used interchangeably with terms such as modification, modified protein, mutant, mutein, divergent, variant, etc., and is not limited as long as the terms are used to indicate mutation.

The variants may also include deletion or addition of amino acids that have minimal influence on the properties and secondary structure of a polypeptide. For example, the variants may be conjugated with a signal (or leader) sequence at the N-terminus involved in the translocation of proteins co-translationally or post-translationally. Further, the polypeptides may also be conjugated with another sequence or linker to identify, purify, or synthesize the polypeptides.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue.

Throughout the entire specification of the present disclosure, the conventional one-letter and three-letter codes for naturally occurring amino acids are used. Additionally, the amino acids mentioned herein are abbreviated according to the nomenclature rules of the IUPAC-IUB as follows:

| | | | |
|---|---|---|---|
| alanine | Ala, A | arginine | Arg, R |
| asparagine | Asn, N | aspartic acid | Asp, D |
| cysteine | Cys, C | glutamic acid | Glu, E |
| glutamine | Gln, Q | glycine | Gly, G |
| histidine | His, H | isoleucine | Ile, I |
| leucine | Leu, L | lysine | Lys, K |
| methionine | Met, M | phenylalanine | Phe, F |
| proline | Pro, P | serine | Ser, S |
| threonine | Thr, T | tryptophan | Trp, W |
| tyrosine | Tyr, Y | valine | Val, V |

Meanwhile, any amino acid may be described as Xaa or X.

Additionally, three-letter codes generally allowed not only for naturally occurring amino acids, but also for other amino acids, such as 2-aminoisobutyric acid (Aib), Sar (N-methylglycine), α-methyl-glutamic acid, etc., may be used.

Amino acids may generally be classified based on similarity of polarity, charge, solubility, hydrophobicity, hydrophilicity, and/or amphipathic nature of a residue. Accordingly, amino acid substitution may generally occur based on similarity of polarity, charge, solubility, hydrophobicity, hydrophilicity, and/or amphipathic nature of a residue.

For example, among the amino acids having an electrically charged side chain (electrically charged amino acid), positively charged (basic) amino acids include arginine, lysine, and histidine; and negatively charged (acidic) amino acids include glutamic acid and aspartic acid. In addition, among the amino acids having an uncharged side chain (uncharged amino acid), nonpolar amino acids include glycine, alanine, valine, leucine, isoleucine, methionine, phenylalanine, tryptophan, and proline; polar or hydrophilic amino acids include serine, threonine, cysteine, tyrosine, asparagine, and glutamine; and among the nonpolar amino acids, aromatic amino acids include phenylalanine, tryptophan, and tyrosine.

As used herein, the term "gene" means a polynucleotide that encodes a polypeptide and a polynucleotide including regions upstream and downstream of the coding region. In some embodiments, a gene may have a sequence (intron) inserted between each coding region (exon).

As used herein, the term "homology" or "identity" refers to a degree of relatedness between two given amino acid sequences or nucleotide sequences, and may be expressed as a percentage. The terms homology and identity may often be used interchangeably with each other.

The sequence homology or identity of conserved polynucleotides or polypeptides may be determined by standard alignment algorithms and can be used with a default gap penalty established by the program being used. Substantially, homologous or identical sequences may generally hybridize under moderately or highly stringent conditions to the full length of the sequence or at least about 50%, 60%, 70%, 80%, or 90% or more of the full length. It is apparent that hybridization with polynucleotides containing general codon or degenerate codons in hybridizing polynucleotides is also included.

Whether any two polynucleotide or polypeptide sequences have a homology, similarity, or identity may be, for example, determined by a known computer algorithm such as the "FASTA" program (Pearson et al., (1988) *Proc. Natl. Acad. Sci. USA* 85:2444) using default parameters. Alternatively, it may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277) (version 5.0.0 or later) (GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST or ClustalW of the National Center for Biotechnology Information (NCBI).

The homology, similarity, or identity of polynucleotides or polypeptides may be, for example, determined by comparing sequence information using, for example, the GAP computer program, such as Needleman et al. (1970), *J Mol Biol.* 48:443 as disclosed in Smith and Waterman, *Adv. Appl. Math* (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unitary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have a homology, similarity or identity with each other may be identified by comparing the sequences in a Southern hybridization experiment under stringent conditions as defined, and appropriate hybridization conditions defined are within the skill of the art, and may be determined by a method well known to those skilled in the art (e.g., J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York), but is not limited thereto.

As used herein, the term "mature polypeptide" means a polypeptide in a form without a signal sequence or propeptide sequence. A mature protein/polypeptide/peptide may be a functional form of a protein/polypeptide/peptide. The mature polypeptide may be in a final form after translation or post-translational modification. Examples of the post-translational modification include N- or C-terminal modifications, glycosylation, phosphorylation, leader sequence removal etc., but are not limited thereto.

As used herein, the term "nucleic acid construct" refers to a single- or double-stranded nucleic acid molecule, which includes one or more regulatory sequences, and which is artificially synthesized, or engineered to include a specific sequence in a manner that does not exist in nature, or isolated from nature.

As used herein, the term "expression" includes any step involved in the production of a polypeptide, e.g., transcription, post-transcriptional modification, translation, post-translational modification, and secretion, etc. but is not limited thereto.

As used herein, the term "expression vector" refers to a linear or circular nucleic acid molecule including a coding sequence and an operably linked regulatory sequence for expression thereof.

As used herein, the term "operably linked" refers to a constitution of placing a regulatory sequence to an appropriate position to regulate expression of a coding sequence. Thus, the term "operably linked" includes an attachment or linking between a regulatory region of a functional domain having a known or desired activity such as a promoter, a stop codon, a signal sequence, or an enhancer, and a target (gene or polypeptide) such that the expression, secretion, or function of the target may be regulated in accordance with the known or desired activity.

As used herein, the term "cDNA" refers to a DNA sequence which can be prepared by reverse transcription from a mature, spliced mRNA molecule obtained from a eukaryotic or prokaryotic cell. The cDNA sequence lacks intron sequences that can be present in the corresponding genomic DNA. The initial primary RNA transcript is a precursor to mRNA which is processed through a series of steps including splicing before appearing as mature spliced mRNA.

As used herein, the term "regulatory sequence" refers to a polynucleotide sequence necessary for the expression of a coding sequence. Each regulatory sequence may be native (derived from the same origin) or foreign (derived from different genes) to the coding sequence. Examples of the regulatory sequence may include a leader sequence, a polyadenylation sequence, a pro-peptide sequence, a promoter, a signal peptide sequence, an operator sequence, a sequence encoding a ribosome-binding domain, and a sequence regulating the termination of transcription and translation. The minimum units of the regulatory sequence may include a promoter, and a sequence for terminating transcription and translation.

In order to describe the variants provided in the present disclosure, the following nomenclature is used.

In the present disclosure, referring to a specific position in an amino acid sequence may include referring to an amino acid present or substituted at that position. Referring to an amino acid at a specific position can be described in various ways. For example, the "position 004" can be described as "position 4", "amino acid 4", "4th amino acid". Additionally, for example, when the amino acid at position 4 is serine (S), it may be described as "S4" or "Ser4".

Amino acid substitution can be expressed by describing the amino acid before substitution, the position, and the amino acid to be substituted in order. The amino acids can be expressed using the conventional one-letter and three-letter codes. In one example, when glutamine, an amino acid at position 202 of a specific sequence, is substituted with leucine, it may be described as "Q202L" or "Gln202Leu".

Any amino acid at a specific position may be referred to as "X". For example, X7 refers to any amino acid at position 7. In addition, when the amino acid to be substituted is expressed as X, it means that it is substituted with an amino acid different from the amino acid present before substitution. For example, "V7X" indicates that V at position 7 is substituted with any amino acid other than V.

Different alterations can be expressed by simultaneously describing several types of amino acids using symbols, such as "/" or ",". For example, when the amino acid (S) at position 135 is substituted with E or P, it may be described in combination of S135E/P or S135E,P. As another example, P/S197K means that the amino acid P or S at position 197 before substitution is substituted with K.

Multiple mutations can be described using "+". For example, descriptions such as "S135P+Q202L" mean that serine, an amino acid at position 153, is substituted with proline, and glutamine, an amino acid at position 202, is substituted with leucine, respectively.

Deletion of an amino acid can be expressed by describing the amino acid before deletion, the position, and * in order. For example, when alanine, an amino acid corresponding to position 8 of a specific sequence, is deleted, it can be expressed as A8* or (Ala8*).

Insertion of an amino acid may be, for example, described as Gly8GlyLys or G8GK, when lysine is inserted between glycine at position 8 and the amino acid at position 9 in a specific sequence. When one or more amino acids are inserted, for example, insertion of lysine and valine between glycine at position 8 and the amino acid at position 9 in a specific sequence can be described as Gly8GlyLysVal or G8GKV. In this case, the position of the inserted amino acid can be indicated using the amino acid number and alphabet in front of the inserted amino acid. For example, in the case described above, the inserted lysine and valine can be numbered as 8aK and 8bV.

As used herein, the term "corresponding to" refers to an amino acid residue at the position recited in a protein or peptide, or an amino acid residue which is similar, identical, or homologous to the residue recited in a protein or peptide. Identifying an amino acid at a corresponding position may be determining a particular amino acid in a sequence that refers to a particular sequence. As used herein, the "corresponding region" generally refers to a similar or corresponding position in the related protein or reference protein.

In the present disclosure, the SEQ ID NO: 1 can be used as a reference sequence to determine the position of amino acids in any amino acid sequence.

That is, the SEQ ID NO: 1 disclosed herein can be used to determine the corresponding amino acid residues in any polypeptide having lysozyme activity. Unless indicated otherwise in the present disclosure, residues of a particular amino acid sequence are numbered relative to SEQ ID NO: 1.

For example, any amino acid sequence is aligned with SEQ ID NO: 1, and based on the alignment, each amino acid residue of the amino acid sequence can be numbered with reference to the numerical position of the amino acid residue corresponding to the amino acid residue of SEQ ID NO: 1. For example, a sequence alignment algorithm such as that described herein can identify the position of an amino acid or a position where modifications such as substitutions, insertions or deletions occur compared to a query sequence (also referred to as a "reference sequence").

An example of the alignment may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277), etc., but is not limited thereto.

Additionally, identification of the corresponding amino acid residue in another lysozyme can be determined by multiple sequence alignment. Examples of the multiple sequence alignment known in the art include, but are not limited to, programs such as MUSCLE (multiple sequence comparison by log-expectation; version 3.5 or later; Edgar, 2004, *Nucleic Acids Research* 32:1792-1797), MAFFT (version 6.857 or later; Katoh and Kuma, 2002, *Nucleic Acids Research* 30:3059-3066; Katoh et al., 2005, *Nucleic Acids Research* 33:511-518; Katoh and Toh, 2007, *Bioinformatics* 23:372-374; Katoh et al., 2009, *Methods in Molecular Biology* 537:39-64; Katoh and Toh, 2010, *Bioinformatics* 26:1899-1900), and EMBOSS EMMA employing ClustalW (1.83 or later; Thompson et al., 1994, *Nucleic Acids Research* 22:4673-4680) using their respective default parameters.

In addition, when enzymes diverged from the mature polypeptide of SEQ ID NO: 1 fail to detect their relationship by traditional sequence-based comparison, other pairwise sequence comparison algorithms can be used (Lindahl and Elofsson, 2000, *J. Mol. Biol.* 295:613-615). Greater sensitivity in sequence-based searching can be attained using search programs that utilize probabilistic representations of polypeptide families (profiles) to search databases. For example, the PSI BLAST program generates profiles through an iterative database search process and is capable of detecting remote homologs (Atschul et al., 1997, *Nucleic Acids Res.* 25:3389-3402). Even greater sensitivity can be achieved if the family or superfamily for the peptide has one or more representatives in the protein structure databases. Programs such as GenTHREADER (Jones, 1999, J. Mol. Biol. 287:797-815; McGuffin and Jones, 2003, *Bioinformatics* 19:874-881) utilize information from a variety of sources, such as PSI BLAST, secondary structure prediction, structural alignment profiles, and solvation potentials, as input to a neural network that predicts the structural fold for a query sequence. Similarly, the method of Gough et al., 2000, *J. Mol. Biol.* 313:903-919 can be used to align a sequence of unknown structure with the superfamily models present in the SCOP database. These alignments can be used in sequence to generate homology models for the peptides, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33:88-96) or combinatorial extension (Shindyalov and Bourne, 1998, *Protein Engineering* 11:739-747), and implementation of these algorithms can additionally be utilized to query structure databases with a structure of interest in order to discover possible structural homologs (Holm and Park, 2000, *Bioinformatics* 16:566-567).

The above methods are one exemplary, and are not limited thereto.

Hereinafter, the specific embodiments of the present disclosure will be described in more detail.

As used herein, lysozyme is an enzyme that catalyzes a hydrolysis reaction of the β-1,4-glycosidic bond between N-acetylglucosamine and N-acetylmuramic acid (NAM). In one example, lysozyme may also be referred to as "muraminidase" or muramidase. In one example, it may be an enzyme having an EC number of 3.2.1. In one example, it may be an enzyme having an EC number of 3.2.1.17. In one example, it may be an enzyme classified as glycoside hydrolase family 25 (GH25). In one example, it may have β-1,4-N,6-O-diacetylmuramidase activity. However, lysozyme is not limited to the above examples.

In the present disclosure, lysozyme activity can be measured and evaluated using methods known in the art, including the embodiments described herein.

As used herein, the term "parent lysozyme" refers to lysozyme to which a modification is applied to produce the variant or the modified polypeptide of the present disclosure. Specifically, the parent lysozyme, parent enzyme, or parent sequence may be a naturally occurring polypeptide or a wild-type polypeptide, may be a mature polypeptide thereof, and may include a variant or functional fragment thereof, but is not limited thereto, as long as the polypeptide has lysozyme activity and can be a parent of the variant.

The parent lysozyme provided in the present disclosure may be a polypeptide of SEQ ID NO: 1, but is not limited thereto. Additionally, it may be a polypeptide having a sequence identity of about 60%, 70%, 75%, 80%, 85%, 90%, 95%, 96%, 97%, 98% or 99% or more with the polypeptide of SEQ ID NO: 1 as long as it has lysozyme activity, and any polypeptide may be included within the scope of the parent lysozyme as long as it has the same or corresponding activity to the polypeptide consisting of the amino acid sequence of SEQ ID NO: 1.

In one embodiment, the mature polypeptide of the parent lysozyme of the present disclosure may be a polypeptide of SEQ ID NO: 3 or a polypeptide having a sequence identity of about 60%, 70%, 75%, 80%, 85%, 90%, 95%, 96%, 97%, 98%, or 99% or more thereto, but is not limited thereto.

The parent lysozyme of the variant provided herein may be derived from *Pseudogymnoascus* sp., *Oidiodendron* sp., *Metapochonia* sp., *Penicillium* sp., *Paecilomyces* sp., *Pochonia* sp., *Talaromyces* sp., *Metarhizium* sp., *Fusarium* sp., *Xylona* sp., *Aspergillus* sp., *Hamiger* sp., *Heterodermia* sp., *Trichoderma* sp., or *Phialemoniopsis* sp. Specifically, it may be derived from *Pseudogymnoascus* sp.

Meanwhile, the above-described microorganism is an exemplary of microorganisms from which the parent lysozyme provided herein can be derived, and includes those derived from microorganisms taxonomically homologous to the microorganism regardless of the name of the microorganisms.

The above-described microorganisms may be obtained from known microorganism depositary authorities such as ATCC, DSMZ, CBS, NRRL, KCTC, and KCCM.

As used herein, a sequence "derived from" a specific microorganism is not limited to those naturally produced or producible in that microorganism, but also includes sequences encoded by genes produced and isolated from the microorganism containing the genes.

For example, lysozyme derived from *Pseudogymnoascus* sp. may include not only enzymes having lysozyme activity naturally produced by the microorganisms of *Pseudogymnoascus* sp., but also those produced in other host cells through genetic modifications known in the art (e.g., transformation into a sequence encoding the enzyme).

As used herein, the "modified polypeptide having lysozyme activity" may be a variant of a parent lysozyme.

As used herein, the term "variant of a parent lysozyme" or "lysozyme variant" refers to a protein having lysozyme activity with at least one amino acid different from the amino acid sequence of the parent lysozyme.

The "modified polypeptide having lysozyme activity", "variant of a parent lysozyme" and "lysozyme variant" can be used interchangeably.

The variant provided in the present disclosure may include one or more amino acid modifications in the sequences of the parent lysozyme, while having lysozyme activity. In addition, i) the variant may be a modified polypeptide having a sequence identity of 70% or more and less than 100% with SEQ ID NO: 1; and/or ii) the variant may be a polypeptide encoded by a polynucleotide having a sequence identity of 70% or more and less than 100% with the sequence encoding a mature polypeptide of SEQ ID NO: 1; and/or iii) the variant may be a polypeptide encoded by (a) a mature polypeptide coding sequence of SEQ ID NO: 1, (b) a cDNA thereof, or (c) a polynucleotide that hybridizes to the full-length complement of (a) or (b) under low-stringency conditions, medium-stringency conditions, medium-high-stringency conditions, high-stringency conditions, or very high-stringency conditions; and/or iv) the variant may be a functional fragment of i), ii) or iii) polypeptide having lysozyme activity.

Specifically, the variant provided in the present disclosure includes modification of one or more amino acids in the parent lysozyme sequence while having lysozyme activity, and thus may have one or more modified functions or properties compared to the parent lysozyme.

In one embodiment, the variant provided in the present disclosure includes modification of one or more amino acids in the parent lysozyme sequence while having lysozyme activity, and thus may have one or more modified functions or properties compared to the parent lysozyme, and one or more conservative substitutions.

The variant provided in the present disclosure, being a variant of the parent lysozyme, may be a polypeptide having lysozyme activity.

In one embodiment, the variant provided in the present disclosure may include modifications at one or more positions corresponding to positions 135 and 202 of SEQ ID NO: 1.

In the present disclosure, the position number is a position corresponding to the position of the polypeptide of SEQ ID NO: 1, and the term "corresponding" is as described above.

In one embodiment, the variant provided in the present disclosure may include modifications of amino acids corresponding to one or more of S135 and Q202 of SEQ ID NO: 1.

In one embodiment, before the modification of the variant provided in the present disclosure, the amino acid corresponding to position 135 may be serine (S); and/or the amino acid corresponding to position 202 may be glutamine (Q).

In one embodiment, the variant provided in the present disclosure may include substitution of the amino acid corresponding to position 135 of SEQ ID NO: 1 with G, A, V, L, I, M, F, W, P, T, C, Y, N, Q, D, E, K, R, or H. Specifically, it may include substitution with G, A, V, L, I, M, F, W, or P, and more specifically, substitution with P.

In one embodiment, the variant provided in the present disclosure may include substitution of the amino acid corresponding to position 202 of SEQ ID NO: 1 with G, A, V, L, I, M, F, W, P, S, T, C, Y, N, D, E, K, R, or H. Specifically, it may include substitution with G, A, V, L, I, M, F, W, or P, and more specifically, substitution with L.

In one embodiment, the variant provided in the present disclosure may include substitution of the amino acid corresponding to position 135 of SEQ ID NO: 1 with a non-polar amino acid.

In one embodiment, the variant provided in the present disclosure may include substitution of the amino acid corresponding to position 202 of SEQ ID NO: 1 with a non-polar amino acid.

In one embodiment, the variant provided in the present disclosure may include substitutions of one or more of S135P and Q202L of SEQ ID NO: 1.

In one embodiment, the variant provided in the present disclosure includes all possible combinations of the modifications described above.

For example, the variant may include modifications of amino acids at positions selected from i) to iii) below, by combinations of the modifications described above: i) 135; ii) 202; and iii) 135+202.

In another example, the variant may include any one or more substitutions from i) and ii) below, but is not limited thereto:

i) substitution of an amino acid at position 135 with proline; and ii) substitution of an amino acid at position 202 with leucine.

In still another example, the variant may include any one or more modifications selected from below, but is not limited thereto:

S135P;

Q202L; and

S135P+Q202L.

In one embodiment, the variant provided in the present disclosure may have a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, and less than 100% with the parent lysozyme; a mature polypeptide thereof, or a functional fragment thereof.

In one embodiment, the variant provided in the present disclosure may have a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, and less than 100% with SEQ ID NO: 1.

In one embodiment, the variant provided in the present disclosure may be a polypeptide encoded by a polynucleotide having a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, and less than 100% with a sequence encoding a mature polypeptide of SEQ ID NO: 1.

In one embodiment, the variant provided in the present disclosure may have a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, and less than 100% with a functional fragment of SEQ ID NO: 1.

Among the above-described embodiments, description of amino acids at positions 135 and 202 of SEQ ID NO: 1 may be equally applied to amino acids at positions 118 and 185 of SEQ ID NO: 3, which are amino acids corresponding to the above positions.

In any one of the above-described embodiments, the variant provided in the present disclosure may include substitution of the amino acid corresponding to position 118 of SEQ ID NO: 3 with G, A, V, L, I, M, F, W, P, T, C, Y, N, Q, D, E, K, R, or H. Specifically, it may include substitution with G, A, V, L, I, M, F, W, or P, and more specifically, substitution with P.

In any one of the above-described embodiments, the variant provided in the present disclosure may include substitution of the amino acid corresponding to position 185 of SEQ ID NO: 3 with G, A, V, L, I, M, F, W, P, S, T, C, Y, N, D, E, K, R, or H. Specifically, it may include substitution with G, A, V, L, I, M, F, W, or P, and more specifically, substitution with L.

In any one of the above-described embodiments, the variant provided in the present disclosure may include substitution of the amino acid corresponding to position 118 of SEQ ID NO: 3 with a non-polar amino acid.

In any one of the above-described embodiments, the variant provided in the present disclosure may include substitution of the amino acid corresponding to position 185 of SEQ ID NO: 3 with a non-polar amino acid.

In any one of the above-described embodiments, the variant provided in the present disclosure may include substitutions of one or more of S118P and Q185L of SEQ ID NO: 3.

In any one of the above-described embodiments, the variant provided in the present disclosure includes all possible combinations of the modifications described above.

For example, the variant may include modifications of amino acids at positions selected from i) to iii) below, by combinations of the modifications described above: i) 118; ii) 185; and iii) 118+185 of SEQ ID NO: 3.

In any one of the above-described embodiments, the variant may include any one or more substitutions from i) and ii) below, but is not limited thereto: i) substitution of an amino acid at position 118 with proline; and ii) substitution of an amino acid at position 185 with leucine of SEQ ID NO: 3.

In any one of the above-described embodiments, the variant may include any one or more modifications selected from below based on SEQ ID NO: 3, but is not limited thereto:

S118P;

Q185L; and

S118P+Q185L.

Specifically, in SEQ ID NO: 3, the variant including a mutation corresponding to the S135P substitution of SEQ ID NO: 1 may be represented by SEQ ID NO: 12, and the variant including a mutation corresponding to the Q202L substitution of SEQ ID NO: 1 may be represented by SEQ ID NO: 13, and a variant including a mutation corresponding to the S135P+Q202L substitution of SEQ ID NO: 1 may be represented by SEQ ID NO: 14.

In the variant provided in the present disclosure, one or more of any selectable or detectable properties or attributes of a polypeptide may be altered as compared to other lysozymes, e.g., wild-type lysozyme, parent lysozyme, other lysozyme variants, etc.

The properties or attributes may include, but are not limited to oxidative stability, substrate specificity, catalytic activity, thermal stability, alkaline stability, pH activity profile, resistance to proteolytic degradation, $K_M$, $k_{cat}$, $k_{cat}/K_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat diseases, etc.

In one embodiment, the variant provided in the present disclosure may have increased thermal tolerance and/or thermal stability compared to the parent sequence.

As used herein, the "enzymatic activity" exhibits at least one catalytic activity. Specifically, it may be the conversion efficiency of an enzyme mainly expressed as $k_{cat}/K_M$, but is not limited thereto.

When the enzyme is completely saturated with substrates, $k_{cat}$ means the rate constant (catalytic constant) that converts substrates into products in unit time by one enzyme, and is also referred to as a turnover number. $K_M$ is the substrate concentration when the reaction rate is at half the maximum value ($V_{max}$).

Examples of the ways to express enzymatic activity include specific activity (μmol of converted substrate$\times$mg$^{-1}\times$min$^{-1}$) or volumetric activity (μmol of converted substrate$\times$mL$^{-1}\times$min$^{-1}$), etc.

However, defining the enzymatic activity is not limited to the description described above, and the enzymatic activity can be defined and evaluated based on the information disclosed in the following literature references: Irwin H. Segel, *Enzyme kinetics*, John Wiley & Sons, 1979; A. G. Marangoni, *Enzyme kinetics*, Wiley-Interscience, 2003; A. Fersht, *Enzyme structure and mechanisms*, John Wiley & Sons, 1981; *Structure and Mechanism in Protein Science: A guide to enzyme catalysis and protein folding*, Alan Fersht, W. H. Freeman, 1999; *Fundamentals of Enzyme Kinetics*, Athel Cornish-Bowden, Wiley-Blackwell 2012; and Voet et al., *Biochemie* [*Biochemistry*], 1992, VCH-Verlag, Chapter 13, pages 331-332 with respect to enzymatic activity, etc.

In one embodiment, the variant provided in the present disclosure may have an increased enzymatic activity by about 100%, about 110%, about 120%, about 130%, about 140%, about 150%, about 160%, about 170%, about 180%, about 190%, or about 200% or more as compared to the parent enzyme.

In another embodiment, the variant provided in the present disclosure may have a decreased enzymatic activity by about 99%, about 95%, about 90%, about 80%, about 70%, about 60%, about 50%, about 40%, or about 20% or less as compared to the parent enzyme.

As used herein, the term "specific activity" refers to the activity of an enzyme per unit weight of proteins, and can be expressed as unit/mg. The quantification of proteins can be performed using, for example, SDS-PAGE or Bradford assay.

Enzyme stability means that enzyme activity is maintained during storage or reaction time. In order to measure such changes in stability, the initial enzyme activity can be measured and compared under defined conditions at time zero (100%) and after a certain period of time (x %), and thus, the level at which the enzyme activity is lost or enzyme stability can be expressed.

Factors that affect enzyme activity include, for example, pH, heat, the presence of other substances (e.g., oxidizing agents, chelating agents), etc.

As used herein, the term "pH stability" means the ability of a protein to function in a specific pH range. In one embodiment, the variant provided in the present disclosure may have activity at about pH 4.0 to about pH 12.0, but is not limited thereto.

When a protein maintains its function in a specific pH range, it can be defined as having "pH stability", and can also be defined as having "acid resistance", "alkali resistance", etc. according to the pH range.

As used herein, the term "thermal stability" means the ability of a protein to function in a specific temperature range. In one embodiment, the variant provided in the present disclosure may have activity in the range of about 15° C. to about 100° C., for example, in the range of about 15° C. to about 90° C., about 15° C. to about 80° C., about 15° C. to about 70° C., about 18° C. to about 70° C., about 18° C. to about 65° C., about 18° C. to about 65° C., or about 20° C. to about 60° C., but is not limited thereto.

As used herein, the term "thermal tolerance" means the ability of a protein to function after exposure to a specific temperature, e.g., high heat or cryogenic temperature. For example, proteins that are thermotolerant may not function at a temperature they are exposed to, but may become functional when returned to an optimal temperature environment.

An increase in stability may include maintaining high enzymatic activity; increasing the range of pH, temperature and/or time, etc., at which a protein maintains its function, by comparing to other enzymes, e.g., a wild-type enzyme, parent enzyme and/or other variants.

A decrease in stability may include maintaining low enzymatic activity; decreasing the range of pH, temperature and/or time, etc., at which a protein maintains its function, by comparing to other enzymes, e.g., a wild-type enzyme, parent enzyme and/or other variants.

As used herein, the term "substrate specificity" means the ability of an enzyme to identify a substrate and molecules that compete with the substrate. Substrate specificity can be determined by measuring the activity of an enzyme for different substrates. In one embodiment, the change in substrate specificity may be a change in the direction of increasing specificity for a substrate capable of producing a desired product. In another embodiment, the change in substrate specificity may be a change in a direction of decreasing specificity for a substrate capable of producing a desired product.

The altered properties of the variant provided in the present disclosure may be suitable or improved activity for application in the industrial field in which lysozyme is used, e.g., production and preservation of feeds, foods, detergents, quasi-drugs, cosmetics, and/or pharmaceuticals, etc.

The polynucleotide encoding the variant of the present disclosure may include the coding sequence of the above-described variant. The polynucleotide may undergo various modifications in the coding region within the scope that does not change the amino acid sequence of the polypeptide, due to codon degeneracy or in consideration of the codons preferred in an organism in which the polypeptide is to be expressed.

Additionally, the polynucleotide of the present disclosure may include a probe that may be prepared from a known gene sequence, for example, any sequence encoding the variant of the present disclosure by hybridizing with a sequence complementary to all or part of the nucleotide sequence described above under stringent conditions without limitation.

The "stringent conditions" refers to conditions under which specific hybridization between polynucleotides is allowed. Such conditions are specifically described in the literature (e.g., J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York).

For example, the stringent conditions may include conditions under which polynucleotides having a high homology or identity of 40% or more, specifically 90% or more, more specifically 95% or more, 96% or more, 97% or more, 98% or more, and even more specifically 99% or more are hybridized with each other and polynucleotides having a homology or identity lower than the above homologies or identities are not hybridized with each other, or washing conditions of the conventional Southern hybridization, that is, washing once, specifically twice or three times at a salt concentration and a temperature corresponding to 60° C., 1×SSC, 0.1% SDS, specifically 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenine is complementary to thymine, and cytosine is complementary to guanine. Therefore, the polynucleotide of the present disclosure may include isolated nucleotide fragments complementary to the entire sequence as well as nucleic acid sequences substantially similar thereto.

Specifically, polynucleotides having a homology or identity with the polynucleotide of the present disclosure may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing the polynucleotides depends on the length of the polynucleotides and the degree of complementation, and these variables are well known in the art (see, Sambrook et al., supra, 9.50-9.51, 11.7-11.8).

For example, the "high-stringency" condition may occur at about 5° C. to 10° ° C. below the $T_m$ of the probe; the "medium-stringency" condition may occur at about 10° C. to 20° C. below the $T_m$ of the probe; and the "low-stringency" condition may occur at about 20° ° C. to 25° C. below the $T_m$, but the stringency is not limited thereto.

In one example, the "low-stringency condition" may mean, for probes of at least about 100 nucleotides in length, prehybridization and hybridization at 42° C. in 5×SSPE, 0.3% SDS, 200 μg/mL of sheared and denatured salmon sperm DNA, and 25% formamide, according to the standard Southern blotting procedures for 12 to 24 hours. The carrier material is finally washed two or three times each for 15 minutes in 2×SSC, 0.1% to 0.2% SDS at 50° C.

In one example, the "medium-stringency condition" may mean, for probes of at least about 100 nucleotides in length, prehybridization and hybridization at 42° C. in 5×SSPE, 0.3% SDS, 200 μg/mL of sheared and denatured salmon sperm DNA, and 35% formamide, according to the standard Southern blotting procedures for 12 to 24 hours. The carrier material is finally washed two or three times each for 15 minutes in 2×SSC, 0.1% to 0.2% SDS at 55° C.

In one example, the "medium-high-stringency condition" may mean, for probes of at least about 100 nucleotides in length, prehybridization and hybridization at 42° C. in 5×SSPE, 0.3% SDS, 200 μg/mL of sheared and denatured salmon sperm DNA, and 35% formamide, according to the standard Southern blotting procedures for 12 to 24 hours. The carrier material is finally washed two or three times each for 15 minutes in 2×SSC, 0.1% to 0.2% SDS at 60° C.

In one example, the "high-stringency condition" may mean, for probes of at least about 100 nucleotides in length, prehybridization and hybridization at 42° C. in 5×SSPE, 0.3% SDS, 200 μg/mL of sheared and denatured salmon sperm DNA, and 35% formamide, according to the standard Southern blotting procedures for 12 to 24 hours. The carrier material is finally washed two or three times each for 15 minutes in 2×SSC, 0.1% to 0.2% SDS at 65° C.

The nucleic acid construct provided in the present disclosure may include a polynucleotide encoding the variant provided herein, operably linked to one or more regulatory sequences that direct the expression of the coding sequence in an appropriate host cell under conditions suitable for the regulatory sequences.

The polynucleotides can be engineered in various ways to allow the expression of variants. Depending on the expression vector, it may be desirable or necessary to manipulate the polynucleotides prior to insertion into the vector. Such manipulations may be performed using methods known in the art.

The "vector" provided in the present disclosure refers to a DNA construct containing the nucleotide sequence of a polynucleotide encoding the variant operably linked to a suitable expression regulatory region (expression regulatory sequence) so as to be able to express the variant of the present disclosure in a suitable host cell. The expression regulatory region may include a promoter capable of initiating transcription, any operator sequence for regulating the transcription, a sequence encoding a suitable mRNA ribosome-binding site, and a sequence for regulating termination of transcription and translation. Once transformed into a suitable host cell, the vector may replicate or function independently from the host genome, or may integrate into genome thereof.

The vector that can be used in the present disclosure is not particularly limited, and any vector known in the art may be used. Examples of the vectors typically used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used; and as a plasmid vector, those based on pBR, PUC, pBluescriptII, pGEM, pTZ, pCL, pET, etc. may be used. Specifically, pDZ, pACYC177, pACYC184, pCL, pECCG117, pUC19, pBR322, pMW118, pCC1BAC vector, etc. may be used.

In one example, a polynucleotide encoding the variant provided in the present disclosure may be inserted into the chromosome through a vector for intracellular chromosomal insertion. The insertion of the polynucleotide into the chromosome may be performed by any method known in the art, for example, by homologous recombination, but is not limited thereto. The vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface polypeptides, may be used. Only cells expressing the selection marker are able to survive or show different phenotypes under the environment treated with the selective agent, and thus the transformed cells may be selected.

Any host cell may be included in the host cell of the present disclosure as long as it can express the variant of the present disclosure without limitation.

The host cell of the present disclosure may include the above-described variant, a polynucleotide encoding the variant, a nucleic acid construct and/or vector containing the same.

The nucleic acid construct or vector may be integrated into the chromosome as described earlier, or may remain as a self-replicating extrachromosomal vector.

The host cell of the present disclosure encompasses any progeny of a parent cell that is not identical to the parent cell due to mutations that occur during replication.

The host cell may be any cell useful in the recombinant production of a variant, e.g., a prokaryote or a eukaryote.

The prokaryotic host cell may be any Gram-positive or Gram-negative bacterium.

The Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces.*

The Gram-negative bacteria include, but are not limited to, *Campylobacter, Escherichia coli, Flavobacterium, Fusobacterium, Helicobacter, Ilyobacter, Neisseria, Pseudomonas, Salmonella, Vibrio* (e.g., *Vibrio natriegens*), and *Ureaplasma.*

In one embodiment, the bacterial host cell may be a host cell belonging to the genus *Bacillus*, specifically including *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells, but is not limited thereto.

In one embodiment, the bacterial host cell may be a host cell belonging to the genus *Streptococcus*, specifically including *Streptococcus equisimilis, Streptococcus pyogenes, Streptococcus uberis*, and *Streptococcus equi* subsp. *zooepidemicus*, but is not limited thereto.

In one embodiment, the bacterial host cell may be a host cell belonging to the genus *Streptomyces*, specifically including *Streptomyces achromogenes, Streptomyces avermitilis, Streptomyces coelicolor, Streptomyces griseus*, and *Streptomyces lividans*, but is not limited thereto.

In one embodiment, the bacterial host cell may be a host cell belonging to the genus *Corynebacterium*, and may be *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens*, but is not limited thereto.

The host cell may be a eukaryote, such as a mammalian, insect, plant, or fungal cell.

The host cell may be a fungal cell. As used herein, the "fungi" include Ascomycota, Basidiomycota, Chytridiomycota, and Zygomycota as well as the Oomycota and all mitosporic fungi.

The fungal host cell may be a yeast cell. As used herein, the "yeast" includes ascosporogenous yeast (Endomycetales), basidiosporogenous yeast, and yeast belonging to the Fungi *imperfecti* (Blastomycetes). However, the classification of yeasts may change, and can be defined as described in Biology and Activities of Yeast (Skinner, Passmore, and Davenport, editors, *Soc. App. Bacteriol. Symposium* Series No. 9, 1980).

The yeast host cell may be a *Candida, Hansenula, Kluyveromyces, Pichia, Komagataella, Pichia, Komagataella, Saccharomyces, Schizosaccharomyces*, or *Yarrowia* cell, e.g., *Pichia pastoris, Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Komagataella phaffii*, or *Yarrowia lipolytica.*

The fungal host cell may be a filamentous fungal cell. As used herein, the "filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth by fungi is by hyphal elongation, and carbon catabolism is obligately aerobic. In contrast, vegetative growth by yeasts such as *Saccharomyces cerevisiae* is by budding of a unicellular thallus, and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride*, but is not limited thereto.

The composition of the present disclosure may be used to degrade peptidoglycan.

In one embodiment, the composition of the present disclosure may be used for lysis of bacterial cells containing peptidoglycan as a component of a cell wall. In one embodiment, the composition of the present disclosure may be used to lyse Gram-positive bacteria.

The composition of the present disclosure may further include other components in addition to the variant provided in the present disclosure. The components added to the composition of the present disclosure may be appropriately selected by those skilled in the art.

In one embodiment, the composition of the present disclosure may further include any components suitable for use in degrading peptidoglycan and/or bacterial cells containing the same as a component of a cell wall.

In one embodiment, the composition of the present disclosure may further include any components suitable for application in feeds, foods, detergents, quasi-drugs, cosmetics, and pharmaceuticals, etc.

Examples of materials that may be added include stabilizers, surfactants, builders, chelating agents, dispersants, enzymes, enzyme stabilizers, catalysts, activators, carriers, binders, lubricants, disintegrants, excipients, solubilizers, suspending agents, colorants, flavoring agents, buffers, preservatives, analgesics, solubilizers, isotonic agents, stabilizers, diluents, lubricants, preservatives, etc., but are not limited thereto.

In one embodiment, the composition provided in the present disclosure may further include a naturally occurring material or a non-naturally occurring material, in addition to the variant provided in the present disclosure.

In one embodiment, the composition provided in the present disclosure may further include additional enzymes commonly used in feeds, foods, detergents, quasi-drugs, cosmetics, and pharmaceuticals, etc., in addition to the variant provided in the present disclosure.

For example, the additional enzymes may include any one or more enzymes selected from the group consisting of aminopeptidase, amylase, carbohydrase, carboxypeptidase, cellulase, chitinase, cutinase, cyclodextrin glycosyltransferase, deoxyribonuclease, esterase, galactosidase, glucoamylase, glucosidase, haloperoxidase, invertase, laccase, lipase, mannosidase, oxidase, pectinolytic enzyme, peptideoglutaminase, peroxidase, phytase, polyphenoloxidase, proteolytic enzyme, ribonuclease, transglutaminase and/or other enzymes useful in a commercial process in conjunction with xylanase.

The method for preparing the variant of the present disclosure may include culturing a host cell.

As used herein, the term "cultivation" means that the host cell is grown under appropriately controlled environmental conditions. The cultivation process of the present disclosure may be performed in a suitable culture medium and culture conditions known in the art. Such a cultivation process may be easily adjusted for use by those skilled in the art according to the strain to be selected. Specifically, the cultivation may be a batch culture, a continuous culture, and a fed-batch culture, but is not limited thereto.

As used herein, the term "medium" refers to a mixture of materials which contains nutrient materials required for the cultivation of the host cell as a main ingredient, and it supplies nutrient materials and growth factors, along with water that is essential for survival and growth. Specifically, the medium and other culture conditions used for culturing the host cell of the present disclosure may be any medium used for conventional cultivation of host cells without any particular limitation. However, the host cell of the present disclosure may be cultured under aerobic conditions in a conventional medium containing an appropriate carbon source, nitrogen source, phosphorus source, inorganic compound, amino acid, and/or vitamin, while adjusting temperature, pH, etc.

In the present disclosure, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; amino acids, such as glutamic acid, methionine, lysine, etc. Additionally, the carbon source may include natural organic nutrients such as starch hydrolysate, molasses, blackstrap molasses, rice bran, cassava, sugar cane molasses, and corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition product thereof, defatted soybean cake or decomposition product thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compounds may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch or continuous manner, but these phosphorus sources are not limited thereto.

Additionally, the pH of the medium may be adjusted by adding a compound such as ammonium hydroxide, potassium hydroxide, ammonia, phosphoric acid, sulfuric acid, etc. during the cultivation of the host cell in an appropriate manner. In addition, bubble formation may be prevented during the cultivation using an antifoaming agent such as fatty acid polyglycol ester. Further, oxygen gas or a gas containing oxygen may be injected to the medium order to maintain aerobic conditions of the medium; or nitrogen gas, hydrogen gas, or carbon dioxide may be injected to maintain anaerobic or microaerobic conditions, without the injection of gas, but the gas is not limited thereto.

The temperature during the cultivation of the present disclosure may be in the range from 20° C. to 40° C., specifically from 25° C. to 37° C., but is not limited thereto. The cultivation may be continued until the desired amount of a useful material is obtained, and may be specifically carried out for 10 to 120 hours, but is not limited thereto.

In one embodiment, the method for preparing the modified polypeptide having lysozyme activity of the present disclosure may further include recovering the modified polypeptide having lysozyme activity of the present disclosure expressed in the culturing step.

In another embodiment, the variant expressed in the culturing step may be recovered using methods known in the art to which the present disclosure pertains. For example, the variant may be recovered from a nutrient medium by conventional procedures including, but not limited to, collection, centrifugation, filtration, extraction, spray-drying, evaporation, or precipitation.

In the recovering step, the variant may be collected using the method of culturing the host cell of the present disclosure, for example, using a suitable method known in the art according to a batch culture, continuous culture, or fed-batch culture method. For example, methods such as centrifugation, filtration, treatment with a protein crystallizing precipitant (salting-out method), extraction, ultrasonic disruption, ultrafiltration, dialysis, various kinds of chromatography such as molecular sieve chromatography (gel filtration), adsorption chromatography, ion exchange chromatography, affinity chromatography, etc., HPLC, and a combination thereof may be used, and the variant can be recovered from the medium or the host cell using suitable methods known in the art.

In still another embodiment, the variant expressed by the host cell in the culturing step may not be recovered. In the embodiment, the host cell expressing the variant may be used as a source of the variant.

Peptidoglycan can be hydrolyzed using the variant of the present disclosure, a host cell expressing the same, and a composition including the variant and/or the host cell. In addition to the variant of the present disclosure, cofactors, coenzymes, etc. may be added in combination in the hydrolysis step of peptidoglycan. The hydrolysis step of peptidoglycan may be performed under optimal pH, temperature conditions, etc., and appropriate conditions can be selected by those skilled in the art.

The variant of the present disclosure may be used in food and feed compositions. The variant of the present disclosure may be used, for example, as antibacterial agents, preservatives or antiseptic agents in the composition. For example, the variant of the present disclosure may be included for the purpose of preventing food or feed from spoilage or deterioration by microorganisms, but is not limited thereto.

The variant of the present disclosure may be used in pharmaceutical and quasi-drug compositions. Lysozyme is known to have antibacterial activity, antiviral activity, anti-inflammatory activity, anticancer activity and/or immune enhancing effect, and the variant of the present disclosure may be included in pharmaceutical or quasi-drug compositions used for the improvement or treatment of bacteria, viruses, inflammation, immune-related diseases and/or cancer. As another example, the variant of the present disclosure may be included, for example, as an antibacterial agent, preservative or antiseptic agent in the pharmaceuticals or quasi-drugs, but is not limited thereto.

The variant of the present disclosure may be used in cosmetics. For example, the variant of the present disclosure may be included in cosmetic compositions having functions such as wound healing, cell regeneration, improvement or treatment of acne, etc. As another example, the variant of the present disclosure may be included as an antibacterial agent, preservative or antiseptic agent in the cosmetics, but is not limited thereto.

The variant of the present disclosure may be used in detergent compositions. The detergent composition may be used, for example, for cleaning fabrics or hard surfaces. For example, the detergent composition including the variant of the present disclosure may further include a proteolytic enzyme, but is not limited thereto.

EXAMPLES

Hereinafter, the present disclosure will be described in more detail by way of Examples and Experimental Examples. However, these Examples and Experimental Examples are provided for illustrative purposes only, and the scope of the present disclosure is not intended to be limited by these Examples and Experimental Examples.

Example 1: Preparation of Lysozyme Variant Plasmids

SEQ ID NO: 2, a nucleic acid sequence encoding the hypothetical protein V493_06130 (KFY23058.1, SEQ ID NO: 1, hereinafter referred to as Ps_Lys) of the *Pseudogymnoascus* sp. VKM F-4281 strain, was synthesized. The vector was amplified by PICZ_F, PICZ_R primer pair using Pfu-X (Solgent), the insert was amplified by Ps_Lys_F, Ps_Lys_R primer pair using Pfu-X (Solgent), and cloned into pPICZα (Invitrogen) using an In-Fusion HD cloning kit (Takara, Cat. No. 639650) to prepare a plasmid, and the plasmid identified through sequencing was named pPICZ_Ps_Lys.

Plasmids for substituting serine at position 118 with proline (S118P) and glutamine at position 185 with leucine (Q185L) based on the mature protein (SEQ ID NO: 3) for the introduction of a point mutation of Ps_Lys were prepared.

pPICZ_Ps_Lys was amplified by Ps_Lys_F, S118P_R primer pair and S118P_F, Ps_Lys_R primer pair for pPICZ-Ps_Lys_S118P and by Ps_Lys_F, Q185L_R primer pair and Q185L_F, Ps_Lys_R primer pair for pPICZ-Ps_Lys_Q185L, cloned into pPICZ vector and confirmed through sequencing.

TABLE 1

| Mutation | Name | SEQ ID NO: | Primer (5' → 3') |
|---|---|---|---|
| | PICZ_F | 4 | TGAGTTTGTAGCCTTAGACATGAC |
| | PICZ_R | 5 | AGCTTCAGCCTCTCTTTTCTC |
| | Ps_Lys_F | 6 | AAGAGAGGCTGAAGCT ACACCTGCTTCACTTGAGAAG |
| | Ps_Lys_R | 7 | TAAGGCTACAAACTCA ACCAAGCGCGATCTTTTTAAG |
| S118P | S118P_F | 8 | GTTTCGGTATAccaCAGTCGGC |
| | S118P_R | 9 | GCCGACTGtggTATACCGAAAC |
| Q185L | Q185L_F | 10 | GTGGGCGTTTttgACAATATGG |
| | Q185L_R | 11 | CCATATTGTcaaAAACGCCCAC |

Example 2: Preparation and Cultivation of *Pichia Pastoris* Strains for Introducing Lysozyme Variants The plasmids of pPICZ_Ps_Lys, pPICZ_Ps_Lys_S118P, and pPICZ_Ps_Lys_Q185L prepared in Example 1 were linearized with restriction enzyme PmeI, transformed into *Pichia pastoris* BG10 strain by electrophoresis, and selected in YPD+zeocin medium (Invitrogen). The selected colonies were seed cultured overnight (O/N) in BMGY medium (1 g/L glycerol, 10 g/L yeast extract, 20 g/L peptone, 100 mM potassium phosphate (pH 6.0), 3.4 g/L YNB (yeast nitrogen base; without amino acid, ammonium sulfate), and 10 g/L ammonium sulfate) and inoculated into 20 mL of BMGY at 1% (v/v). Thereafter, 600 μL of methanol was injected twice every 24 hours. Only the culture solution from which the strains were removed through double centrifugation was used for activity evaluation.

Example 3: Evaluation of Lysozyme Activity

Lysozyme activity was measured by incubating *Micrococcus luteus* with lysozyme (KCTT 3063, ATCC 4698) at room temperature (20° C.) for 5 minutes, and in water bath at 55° C., 60° C. for 5 minutes, then cooling on ice for 5 minutes and measuring the decrease in optical density (OD540) using a spectrophotometer.

The specific method is as follows: *Micrococcus luteus* was seed cultured overnight (O/N) in TSB (Bacto™ Tryptic soy broth, 211825) medium and inoculated 1% into 10 mL TSB medium and cultured overnight (O/N). The strain was harvested through centrifugation, washed twice with distilled water, and a substrate solution was prepared with citric acid-phosphate buffer (pH 6.5) so that $OD_{540}$=1.0.5 μL of the *Pichia* culture medium was added to 200 μL of the substrate in a 96-well plate to initiate the reaction, and the $OD_{540}$ was measured for 1 hour at 5-minute intervals using a microplate reader.

The measured residual activity of the enzyme is shown in Table 2 and FIG. 1 below.

TABLE 2

| | Room temperature (20° C.) | 55° C. | 60° C. |
|---|---|---|---|
| Wild type | 100% | 68.7% | 2.4% |
| S118P | 100% | 74.3% | 2.3% |
| Q185L | 100% | 87.0% | 24.8% |

When the *Pichia* culture solution in which a mutation was introduced into lysozyme Ps_Lys was heat-treated at 60° C. for 5 minutes, the residual activity was higher than that of the control (room temperature). In contrast, the *Pichia* culture solution introduced with Ps_Lys (wild-type mature form) showed 2.4% residual activity when heat-treated at 60° C. for 5 minutes. Therefore, it was confirmed that the thermal stability was improved when the Ps_Lys mutation was introduced compared to the wild type.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified polypeptide comprising an amino acid sequence having at least 90% but less than 100% sequence identity to SEQ ID NO: 1, wherein the modified polypeptide comprises at least one amino acid modification selected from the group consisting of deletion, insertion and substitution at one or more positions corresponding to amino acids 135 and 202 of SEQ ID NO: 1, wherein the amino acid at the position corresponding to position 135 of SEQ ID NO: 1 is not serine(S), wherein the amino acid at the position corresponding to position 202 of SEQ ID NO: 1 is not glutamine (Q), and wherein the modified polypeptide has lysozyme activity.

2. The modified polypeptide of claim 1, wherein the modified polypeptide comprises modifications at both of the positions corresponding to amino acids 135 and 202 of SEQ ID NO: 1.

3. The modified polypeptide of claim 1, wherein an amino acid at a position corresponding to position 135 of SEQ ID NO: 1 is proline.

4. The modified polypeptide of claim 1, wherein the modified polypeptide comprises any one or more modifications selected from below:

S135P;

Q202L; and

S135P+Q202L.

5. The modified polypeptide of claim 1, wherein the modified polypeptide has increased thermal tolerance and/or increased thermal stability compared to an unmodified polypeptide comprising the amino acid sequence as set forth in SEQ ID NO: 1, and wherein the unmodified polypeptide comprises serine at position 135, and/or glutamine at position 202.

6. A method for hydrolyzing peptidoglycan, comprising:

contacting the peptidoglycan with the modified polypeptide of claim 1, a host cell expressing the modified polypeptide, and/or a composition comprising the modified polypeptide.

7. A method for lysing bacteria, comprising:

contacting the modified polypeptide of claim 1, a host cell expressing the modified polypeptide, and/or a composition comprising the modified polypeptide with bacteria comprising peptidoglycan as a component of the cell wall.

8. The modified polypeptide of claim 1, wherein an amino acid at a position corresponding to position 202 of SEQ ID NO: 1 is Leucine.

9. The modified polypeptide of claim 1, wherein an amino acid at a position corresponding to position 135 of SEQ ID NO: 1 is proline, and an amino acid at a position corresponding to position 202 of SEQ ID NO: 1 is Leucine.

* * * * *